United States Patent [19]

Piran et al.

[11] Patent Number: 5,196,349

[45] Date of Patent: Mar. 23, 1993

[54] IMMUNOASSAYS FOR THYROID HORMONES USING THYROGLOBULIN

[75] Inventors: Uri Piran, Sharon; Milos Stastny, Ashland, both of Mass.

[73] Assignee: Ciba Cornign Diagnostics Corp., Medfield, Mass.

[21] Appl. No.: 598,570

[22] Filed: Oct. 17, 1990

Related U.S. Application Data

[63] Continuation of Ser. No. 126,660, Dec. 1, 1987, abandoned.

[51] Int. Cl.$^5$ .................. G01N 33/53; G01N 33/543; G01N 33/553

[52] U.S. Cl. .................. 436/500; 435/7.92; 435/7.93; 436/518; 436/523; 436/526; 436/534; 530/386

[58] Field of Search .............. 435/7.92, 7.93; 436/500, 518, 523, 526, 528, 529, 534; 530/386

[56] References Cited

U.S. PATENT DOCUMENTS

| | | | |
|---|---|---|---|
| Re. 32,098 | 3/1986 | Chopra | 436/500 |
| 4,410,633 | 10/1983 | Hertl et al. | 436/500 |
| 4,824,777 | 4/1989 | Cheng et al. | 435/7 |
| 4,966,838 | 10/1990 | Ferrua et al. | 435/7 |

FOREIGN PATENT DOCUMENTS 0246152  4/1987  European Pat. Off. ............ 436/500

OTHER PUBLICATIONS

Tao, et al., Chemical Abstracts, 94:61029d, 1981.

*Primary Examiner*—David M. Naff
*Attorney, Agent, or Firm*—Arthur S. Morgenstern; Nicholas I. Slepchuk, Jr.

[57] ABSTRACT

Immunoassays for measuring thyroid hormones such as thyroxine($T_4$) and triiodothyronine($T_3$) are carried out by incubating a serum sample with either (a) unlabeled thyroglobulin and a labeled antibody to a thyroid hormone or to thyroxine binding globulin(TBG), or (B) labeled thygloublin and an unlabeled antibody to a thyroid hormone. The thyroglobulin may be immobilized on an insoluble carrier and the immobilized thyroglobulin is preferably modified by succinylation with succinic anhydride. Whole thyroglobulin can be used or the thyroglobulin can be fragmented into smaller peptides prior to use provided the peptides contain at least one $T_3$ or $T_4$ residue per peptide. Preferably, the antibody is a monocional antibody and labeling is with an acridinium ester.

2 Claims, 8 Drawing Sheets

IMMUNOASSAYS FOR THYROID HORMONES USING THYROGLOBULIN

This is a continuation of copending application(s) Ser. No. 07/126,660 filed on Dec. 1, 1987, now abandoned.

FIELD OF THE INVENTION

This invention relates to a novel method for performing binding assays using thyroglobulin. In particular, this invention relates to a novel method for measuring certain hormones in a sample serum using thyroglobulin. More particularly, this invention relates to immunoassays for thyroxine ($T_4$) and triiodothyronine ($T_3$) using thyroglobulin.

BACKGROUND OF THE INVENTION

The determination of the concentrations of thyroid hormones in a patient's serum provides a means for the assessment of the thyrometabolic state of the patient. Several assays are known for the measurement, directly or indirectly, of these hormones, such as total $T_4$, total $T_3$, free $T_4$, free $T_3$, $T_3$ Uptake, among others. Commercially available kits for measuring thyroid hormones include MAGIC® $T_4$ RIA, MAGIC® $T_3$ RIA, MAGIC® F-$T_4$ RIA, MAGIC® F-$T_3$ RIA, and MAGIC® $T_3$-Uptake (available from Ciba Corning Diagnostics Corp., Medfield, Mass.). Copending U.S. application Ser. No. 071,661, filed on Jul. 8, 1987, now issued as U.S. Pat. No. 4,824,777, discloses a method for determining the T-Uptake of a sample serum using solid-phase $T_4$ and labeled anti-thyroxine binding globulin antibody.

Several binding assay configurations for thyroid hormones, including T- or $T_3$-Uptake assays, employ conjugates of $T_4$ or $T_3$ with proteins. In some assay configurations the protein itself is the label, such as an enzyme, fluorescent protein, chemiluminescent protein, or an apoenzyme. In other configurations the protein serves as a spacer that indirectly connects the $T_4$ or $T_3$ to the label, which label can be an enzyme, liposome, chemiluminescent marker, fluorescent marker, latex particle, erythrocyte, etc. Additional assay configurations utilize unlabeled protein-hormone conjugates either as liquid-phase reagents or as solid-phase immobilized reagents, in conjunction with labeled antibody. In some assay configurations both the conjugate and the binder (antibody or thyroxine binding globulin [TBG] or receptor) are not labeled, and the reaction between them is detected by a secondary label, such as an antibody conjugate or by physical-chemical methods.

Preparation of $T_4$ and/or $T_3$ protein conjugates for these assay configurations by chemical synthesis suffers from several problems, such as, e.g., (1) instability of the prepared conjugates because the hormone leaches off the proteins; or (2) production of heterogeneous conjugates that are difficult to reproduce; or (3) poor definition of the prepared conjugates with respect to the number of hormones per protein, the location of the hormones on the protein, and the extent of side reactions that lead to unstable or otherwise undesireable linkages.

Immunoassay configurations involving solid-phase immobilized haptens (such as, e.g., $T_4$ or $T_3$) and labeled antibodies offer certain advantages over other immunoassay configurations. One such advantage is the ability to label the antibodies with markers that are too bulky or too hydrophobic or too large in size, to effectively label haptens. In addition this configuration allows the use of a "non-competitive immunoassay" format. In this format a large excess of labeled antibody first reacts with an analyte followed by adsorbtion of any unreacted label by the solid phase hapten and subsequent measurement of the remaining analyte-bound, liquid-phase label. Solid phase-immobilized haptens often suffer from poor stability because the haptens frequently leach off the solid phase. This stability problem is particularly severe in immunoassays for $T_4$ and $T_3$. Such leaching also presents a potential stability problem when the hapten is coupled to liquid phase proteins or other polymers, or to labels, such as enzymes, liposomes, chemiluminescent markers, bioluminescent markers, latex particles, etc.

It is the purpose of this invention to provide a novel method for performing a binding assay using thyroglobulin. In particular, it is the purpose of this invention to provide a method for, directly or indirectly, measuring certain hormones in a sample serum using thyroglobulin. More particularly, it is the purpose of the present invention to provide a method for measuring certain hormones, such as $T_4$ and $T_3$, in a sample serum using thyroglobulin to help alleviate stability problems and to provide a reproducible, well defined and easily obtainable alternative to chemically produced protein-thyroid hormone conjugates.

DESCRIPTION OF THE INVENTION

Figure 1:
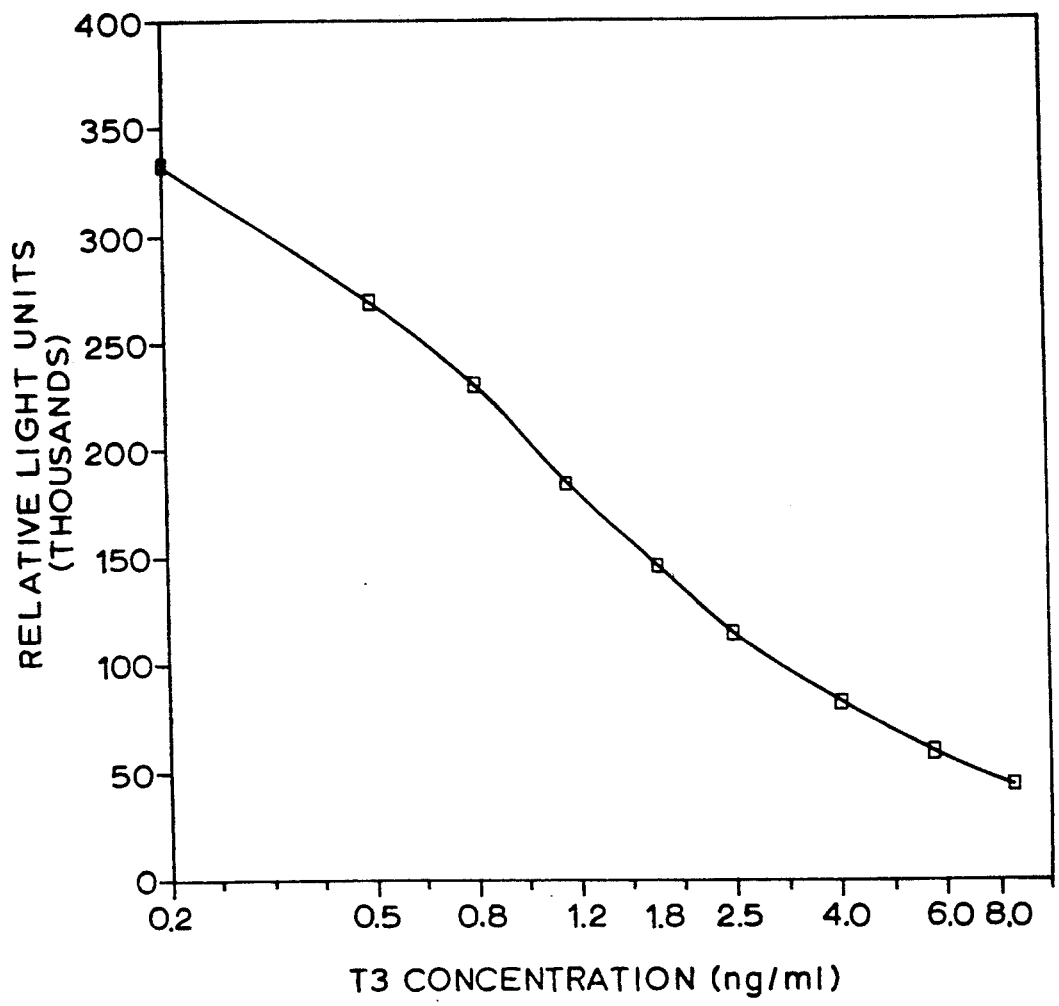
FIG. 1 is a standard curve of a total $T_3$ assay obtained using immobilized thyroglobulin and an acridinium ester labeled anti-$T_3$ antibody.

This invention relates to a method for performing a solid phase binding assay which comprises:
a) incubating a sample serum with:
  i) labeled antibody to a thyroid hormone or labeled antibody to thyroxine binding globulin (TBG), and a composite comprising thyroglobulin immobilized on an insoluble carrier material; or
  ii) labeled thyroglobulin and a composite comprising antibody to a thyroid hormone immobilized on an insoluble carrier material, to form a complexed composite;

b) separating the complexed composite from unbound labeled antibody or unbound labeled thyroglobulin; and c) measuring the amount of label associated with the complexed composite.

This invention also relates to a method for performing a liquid phase binding assay which comprises:

a) incubating a sample serum with:
   i) labeled antibody to a thyroid hormone or a labeled antibody to TBG and unlabeled thyroglobulin; or
   ii) labeled thyroglobulin and unlabeled antibody to a thyroid hormone, to form an antibody-analyte complex;

b) separating the antibody-analyte complex from unbound labeled antibody or unbound labeled thyroglobulin; and c) measuring the amount of label associated with the antibody-analyte complex.

This invention further relates to a method for performing a homogeneous binding assay which comprises:

a) incubating a sample serum with:
   i) a labeled antibody to a thyroid hormone or a labeled antibody to TBG and unlabeled thyroglobulin; or
   ii) labeled thyroglobulin and unlabeled antibody to a thyroid hormone, to form an antibody-analyte complex; and b) measuring the amount of label associated with the antibody-analyte complex.

This invention preferably relates to a method for measuring a thyroid hormone, preferably $T_4$ or $T_3$, in a sample serum which comprises:

a) incubating the sample serum with:
   i) a labeled antibody to the hormone and a composite comprising thyroglobulin immobilized on an insoluble carrier material; or
   ii) labeled thyroglobulin and a composite comprising an antibody to the hormone immobilized on an insoluble carrier material, to form a complexed composite;

b) separating the complexed composite from unbound labeled antibody or unbound labeled thyroglobulin;

c) measuring the amount of label associated with the complexed composite; and d) relating the measurement of step c) to the amount of the hormone in the sample serum.

The thyroglobulin can be immobilized on the insoluble carrier material by any procedure which produces an immobilized thyroglobulin capable of being bound by antibodies to thyroid hormones, such as by antibodies to $T_4$ or by antibodies to $T_3$, or being bound by thyroxine binding globulin (TBG), depending on the desired assay. For example, the procedure described by Groman et al, BioTechniques: Mar./Apr., 1985, p. 156–160, is useful in immobilizing the thyroglobulin for the purposes of this invention.

Thyroglobulin is a protein produced by the thyroid gland and serves as a precursor for thyroid hormones. Thyroglobulin contains endogenous triiodothyronyl ($T_3$) and tetraiodothyronyl ($T_4$) residues coupled by internal peptide linkages to certain defined positions in the thyroglobulin polypeptide chains. For the purposes of this invention, the thyroglobulin can be used as a whole protein molecule or the thyroglobulin can be fragmented into smaller peptides prior to use in the method of this invention provided that the peptides contain at least one $T_3$ or $T_4$ residue per peptide. Thyroglobulin can be fragmented using any known procedure which will produce biologically useful peptides, such as by proteolysis, reduction, oxidation, cyanogen bromide cleavage, etc. Accordingly, for the purposes of the specification and the claims, the term "thyroglobulin" shall mean the entire thyroglobulin molecule as well as smaller peptide fragments of thyroglobulin containing at least one $T_3$ or $T_4$ residue.

The thyroglobulin immobilized on the insoluble carrier material can be further chemically modified to increase the immunoreactivity, the stability, or any other characteristic of the solid phase which will enhance the performance of the immobilized thyroglobulin in the assay. A preferred means for modifying the solid phase thyroglobulin is by succinylation with succinic anhydride.

The amount of immobilized thyroglobulin per unit sample can vary depending on the hormone to be assayed and should be determined empirically by titrating the immobilized thyroglobulin against samples with varying known amounts of the hormone to be measured using any known procedure for measuring the amount of hormone in a sample, e.g., by radioimmunoassay (RIA). This titration will determine the amount of immobilized thyroglobulin necessary to distinguish the low end of the physiological range of the hormone to be measured from the upper end of the physiological range of the hormone. Preferably about 0.01 to 100 ug, more preferably, about 0.1 to 10 ug, of thyroglobulin immobilized on the carrier material per 50 ul of sample serum is utilized.

Unlabeled antibody to the hormone to be measured or unlabeled antibody to TBG can be prepared utilizing known methods for preparing antibodies (see, e.g., G. Kohler and C. Milstein, Eur. J. Immunology, vol. 6, 511–519, 1976). The antibody is then purified and labeled by known procedures (e.g., with enzymatic, fluorogenic, radiometric, bioluminescent, liposomal, particulate, chemiluminescent, etc., labels and markers) (see, e.g., Woodhead et al., Clinical Chemistry 29(8), pp. 1474–1479, 1983). Preferably, the antibody is a monoclonal antibody. The antibody is preferably labeled with an acridinium ester. Any suitable acridinium ester can be used in the method of this invention. Useful acridinium esters are disclosed in copending U.S. application Ser. No. 915,527, filed Oct. 6, 1986, now U.S. Pat. No. 4,745,181, herein incorporated by reference. Particularly preferred is 2',6'-dimethyl-4'-(N-succinimidyloxycarbonyl)phenyl acridine-9-carboxylate.

The amount of labeled antibody necessary can be determined empirically by titrating the antibody against samples of varying known amounts of the hormone to be measured or various known amounts of TBG using any known procedure for measuring antibody-hormone or antibody-TBG interaction. This titration will determine the amount of antibody necessary to discriminate the hormone to be measured or TBG at the levels commonly encountered in clinical samples. Preferably, about 0.1 ng to about 1000 ng of labeled antibody per 50 ul of sample serum is utilized.

Alternatively, unlabeled antibody can be immobilized on the insoluble carrier material. This can be accomplished by any procedure which produces an immobilized antibody capable of binding the hormone to be measured, and/or the labeled thyroglobulin. For example, the procedure described by Groman et al, BioTechniques: Mar./Apr., 1985, p. 156–160, is useful for immobilizing an antibody for the purposes of this invention.

The amount of immobilized antibody per unit sample serum can vary depending on the hormone to be assayed and should be determined empirically by titrating the immobilized antibody against samples with varying known amounts of the hormone to be measured using any known procedure for measuring antibody-hormone interaction. This titration will determine the amount of immobilized antibody necessary to distinguish the low end of the physiological range of the hormone to be measured from the upper end of the physiological range of the hormone. Preferably, about 0.2 ng to about 10,000 ng of antibody immobilized on the carrier material per 50 ul of sample serum is utilized.

Thyroglobulin can be labeled by known procedures (e.g., with enzymatic, fluorogenic, radiometric, bioluminescent, liposomal, particulate, chemiluminescent, etc., labels and markers) (see, e.g., a review article on various labels and markers: Schall R. F., and Tenoso H. J., Clinical Chemistry (1981) 27:1157–1164). D. S. Kabakoff in *Enzyme Immunoassay* (pp. 71–104, CRC Press, Inc., 1980) describes a method for coupling small molecules and large macromolecules to enzymes. These methods are suitable for coupling various labels to thyroglobulin. Preferably, thyroglobulin is labeled with an acridinium ester. Any suitable acridinium ester can be used in the method of this invention. Useful acridinium esters are disclosed in copending U.S. application Ser. No. 915,527. Particularly preferred is 2',6'-dimethyl-4'-(N-succidinimidyloxycarbonyl)phenyl acridine-9-carboxylate.

The amount of labeled thyroglobulin necessary can be determined by titrating the labeled thyroglobulin against samples with varying known amounts of the hormone to be measured using any known procedure for measuring the amount of hormone in a sample. Preferably, about 0.1 ng to about 1000 ng of labeled thyroglobulin per 50 ul of sample serum is utilized.

The insoluble carrier material can be any of the known support materials such as cellulose, Sephadex, polystyrene, nylon, polyacrylamide, latex, glass, magnetizable particles like iron oxide particles, etc. Preferably, thyroglobulin or antibody are immobilized onto a high surface area, insoluble carrier material, in particulate form, having an average particle size (e.g., 0.01 to 10 microns) that limits gravimetric settling over th time of incubation. The particle size should preferably be large enough to enable easy and rapid separation using available laboratory procedures.

Paramagnetic particles are a preferred carrier material. These particles comprise a ferric oxide core surrounded by a polymerized silane coating (see, e.g., U.S. Pat. No. 4,554,088). Thyroglobulin or antibody can be immobilized onto the surface of the particles by known procedures in the art, such as, e.g., the procedures decribed in Groman et al, BioTechniques: Mar./Apr., 1985, p. 156–160.

The incubation conditions can vary depending on time, temperature, hormone to be assayed, final incubation volume, etc., but, preferably, the incubation should be conducted for at least 2 minutes at 25° C.

After the incubation, the complexed composite is separated from the incubation medium. The complexed composite is formed on a water-insoluble solid phase which can be separated by conventional means such as sedimentation, centrifugation or magnetism depending on the insoluble carrier material used. In magnetizable particles, separation is preferably conducted by placing the particles in a magnetic field.

In the method of this invention for performing a liquid phase binding assay, both the antibody and thyroglobulin, labeled or unlabeled, are in a liquid phase. The amount of antibody or thyroglobulin per unit sample can be determined using the titration procedure described above for the solid phase assay. Separation of the antibody-analyte complex from the unbound labeled antibody or unbound labeled thyroglobulin can be done using any known useful procedure in the art (see, e.g., U.S. Pat. No. 4,158,547).

In the method of this invention for performing a homogeneous binding assay, no separation is necessary and the amount of antibody-analyte complex is measured directly after incubation. Any known useful procedure for this measurement in the art can be used (see, e.g. U.S. Pat. No. 4,168,207).

The amount of label associated with the complexed composite or the antibody-analyte complex can be determined by at least two methods: 1) direct quantitation of the label associated with the complexed composite or antibody-analyte complex, or 2) indirect quantitation of the label remaining in the incubation medium after separation and then subtracting this amount from the total label offered. The suitable quantitation procedure will depend largely on the label used. For example, when the label used is acridinium ester, direct quantitation of the label associated with the complexed composite or antibody-analyte complex is the preferred method and can be determined in a luminometer by measuring the photons released by the chemiluminescent reaction of the acridinium ester. The signal produced by the photons is measured in relative light units (RLU), which quantitate th : light emitted from the oxidation of the acridinium ester label.

The amount of label determined to be associated with the complexed composite or the antibody-analyte complex in the method of this invention is then used to determine the amount of the hormone to be measured in the sample serum by any useful method known in the art. The specific calculation or procedure for the determination of the amount of the hormone in the sample serum will vary depending on the specific hormone to be assayed, the specific configuration of the assay components, and the specific assay conditions. For example, in the $T_4$ assay a constant amount of labeled reagent (either labeled anti-$T_4$ antibody or labeled thyroglobulin) and solid phase reagent (either solid phase thyroglobulin or solid phase anti-$T_4$ antibody) is added to all the test tubes. A constant volume of a standard is added to each tube varying in $T_4$ concentration from zero to 30 microgram of $T_4$ per deciliter. After the incubation and separation the signal (RLU) generated from each standard is plotted graphically against its respective concentration to produce a "standard curve". The unknown serum samples, which are processed identically to the standards, are measured and their respective concentrations of $T_4$ determined by interpolation off the standard curve. The standard curve can be used as a mathematical formula instead of a graph and the calculations can be performed automatically by the microcomputer used in conjunction with a luminometer.

The calculations for $T_3$, free-$T_4$, free-$T_3$, and T-uptake are performed in a similar way, although the concentrations present in the standards vary according to the specific assay performed.

A total $T_4$ or total $T_3$ assay according to the method of this invention is preferably conducted in the following manner:

a) incubating a sample serum with either:
  i) labeled antibody (anti-$T_4$ or anti-$T_3$) and a composite comprising thyroglobulin immobilized on an insoluble carrier material, in the presence of a blocking agent, preferably 8-anilino-1-naphtalenesulfonic acid (ANS); or
  ii) labeled thyroglobulin and a composite comprising antibody (anti-$T_3$ or anti-$T_4$) immobilized on an insoluble carrier material, in the presence of a blocking agent, preferably ANS, to form a complexed composite;
b) separating the complexed composite from unbound labeled antibody or unbound labeled thyroglobulin;
c) measuring the amount of label associated with the complexed composite; and
d) calculating the concentration of $T_4$ or $T_3$ by relating the measurement of c) to a measurement of a reference standard or set of standards.

Blocking agents (sometimes called deblocking agents) for use in immunoassays for thyroid hormones are described in U.S. Pat. No. 3,911,096, the pertinent portions of which are herein incorporated by reference Essentially, a blocking agent separates thyroid hormones from thyroid hormone binding proteins. Examples of blocking agents include ANS, merthiolate and dilantin. Another method for separating hormone from binding protein is by pretreating the sample with base, such as, e.g., 0.05 M to 2 M NaOH.

A free $T_3$ or free $T_4$ assay is conducted in the same manner as the assay for total $T_3$ or total $T_4$, except that no blocking agent is used.

The amount of hormone in a sample serum is preferably determined by comparing the signal generated by the sample serum to the signal generated by a reference standard or series of standards of known concentration assayed in the same manner as the sample serum and interpolating the results. This type of determination is well known in the art.

A T-Uptake assay is preferably conducted in the following manner:

a) incubating the sample serum with labeled antibody to thyroxine binding globulin and a composite comprising thyroglobulin immobilized on an insoluble carrier material to form a complexed composite;
b) separating the complexed composite from any unbound labeled antibody;
c) measuring the amount of label associated with the complexed composite; and
d) calculating a T-Uptake ratio by relating the measurment of c) to a measurement of a reference standard.

A T-Uptake assay is described in copending U.S. application Ser. No. 071,661, filed Jul. 8, 1987, herein incorporated by reference. This application discloses a preferred method for the calculation of the T-Uptake ratio in step d).

The following examples illustrate the method of this invention.

EXAMPLE 1

Immobilization of Thyroglobulin on Solid Phase

One gram of paramagnetic particles (obtained from Advanced Magnetics, Inc., Cambridge, Mass.) were activated by incubation for 3 hours with 12 ml of 6.5% glutaraldehyde solution. The activated particles were removed from unreacted glutaraldehyde by magnetic separation of the particles and resuspension in 0.01 M sodium phosphate buffer, pH 7.5. The particles were washed by three cycles of resuspension in sodium phosphate buffer, pH 7.5, and magnetic separation. Bovine thyroglobulin, 160 mg, was dissolved in 12 ml of 0.01 M sodium acetate, pH 5.5, and added to the activated particles. After 18 hours incubation at room temperature the particles were magnetically separated and the supernatant was assayed for protein by measuring the absorbance at 280 nm. More than 80% of the thyroglobulin was found to be immobilized on the particles. The particles so prepared were then washed extensively with 0.01 M phosphate buffer, pH 7.4, resuspended in 40 ml of phosphate buffered saline, pH 7.4, containing 0.1% bovine serum albumin and incubated at 50° C. for 3 hours. The particles so prepared were then washed with fresh phosphate buffer and resuspended in the phosphate buffer to a final volume of 40 ml.

EXAMPLE 2

Succinylation of Solid-Phase-Thyroglobulin

Two ml of the immobilized thyroglobulin particles from Example 1 were pelleted by a magnetic separator and the particles were then resuspended in 2 ml of 0.01 M phosphate buffer, pH 7.4. Twenty mg of succinic anhydride were added to the particles to form a reaction mixture and the reaction mixture was then vortex-mixed for 5 minutes. The pH of the reaction mixture was adjusted to 8.0 with 1 N NaOH and the reaction mixture was then incubated for 2 hours at room temperature. The succinylated particles so produced were then washed three times with the phosphate buffer and resuspended in a final volume of 2 ml phosphate buffered saline, pH 7.4, containing 0.1% bovine serum albumin.

The immobilized thyroglobulin was chemically modified by succinic anhydride in order to prevent the possibility of interferences by patient sera anti-thyroglobulin antibodies to and impart a negative charge to the solid phase.

EXAMPLE 3

Co-immobilization of Thyroglobulin and Bovine Gamma Globulin

One gram of paramagnetic particles was washed and activated by glutaraldehyde as described in Example 1. A mixture of 160 mg bovine gamma globulin and 80 mg bovine thyroglobulin were then reacted with the activated particles for 18 hours at room temperature. To this reaction mixture was then added 40 ml of 1 M phosphate buffer, pH 8.0, followed by 8 grams of succinic anhydride. This succinylation step was carried out for 3 hours at room temperature and was followed by buffer washes as in Example 1. The particles in 40 ml phosphate buffered saline containing 0.1% bovine serum albumin were incubated for 60 hours at 50° C. and washed twice with 0.0005 molar ethylenediaminetetraacetic acid (EDTA), pH 7.0. The particles so produced were then incubated in the EDTA solution for 3 hours at 37° C., magnetically separated, washed and stored in 40 ml of phosphate buffered saline containing 0.1% bovine serum albumin.

A second immobilization was performed in an identical manner except that porcine thyroglobulin was used instead of bovine thyroglobulin.

EXAMPLE 4

Labeling of Thyroglobulin with Acridinium Ester

A. Porcine thyroglobulin was dissolved in 0.1 molar sodium phosphate, pH 8.0, containing 0.15 M NaCl to a concentration of 0.25 mg per ml. To 1 ml of this solution was added 0.05 ml of 2',6'-dimethyl-4'-(N-succinimidyloxycarbonyl)phenyl acridine-9-carboxylate (0.4 mg/ml) in dimethylformamide. After 10 minutes incubation at room temperature, 10 mg of succinic anhydride was added and incubation was continued with mixing for another 10 minutes. The reaction was stopped by addition of 0.5 ml of 10 mg/ml solution of DL-lysine, and the labeled thyroglobulin so produced was purified by gel filtration using a 10 ml column of Sephadex G-25. The product emerging at the void volume of the column was collected.

B. Bovine thyroglobulin was labeled by the procedure described in A except that the succinylation step was omitted.

EXAMPLE 5

Assay for $T_3$ Using Immobilized Thyroglobulin

A. Monoclonal anti-$T_3$ antibody was produced in mice (A/J) by immunization with the BSA-$T_3$ conjugate and subsequent fusion of the splenocytes with Sp2/0-Ag 14 myeloma cells by the procedure described by Kohler and Milstein in Nature (London), Vol. 256, pp. 495–497 (1975). Hybridoma cells secreting anti-$T_3$ antibody were injected introperitoneally into pristane-primed mice (CAF). Ascitic fluid from these mice was collected after 3-5 weeks. The anti-$T_3$ antibody was purified from the ascitic fluid by Protein A column chromatography using the Affi-Gel Protein A MAPS II Kit (Bio-Rad Laboratories, Richmond, Calif. 94801) according to the written protocol provided with the kit.

The anti- $T_3$ antibody was labeled with acridinium ester using 2',6',-dimethyl-4'-(N-succidinimidyloxycarbonyl)phenyl acridine-9-carboxylate as the starting acridinium ester. The procedure utilized was as follows:
250 ug of the anti-$T_3$ antibody in 0.1 M sodium phosphate, 0.15 M sodium chloride, pH 8.0, was mixed with 50 ul of 2',6',-dimethyl-4'-(N-succidinimidylcarbonyl)phenyl acridine-9-carboxylate (0.4 mg/ml) in dimethylformamide and incubated for 15 minutes at room temperature. 0.5 ml of a 10 mg/ml solution of DL-lysine was added to the mixture and the mixture was purified by filtration through a 10 ml column of Sephadex G-25. The labeled antibody appeared at the void volume of the column and was eluted.

B. A series of standards (from a MAGIC® $T_3$ RIA Kit, Ciba Corning Diagnostics Corp., Medfield, Mass.) (0.05 ml) with increasing amounts of $T_3$ were added to 12×75 mm plastic tubes. 0.5 ml of the solid phase bovine thyroglobulin prepared in Example 3 (0.25 mg/l in Buffer I containing 0.02 M sodium phosphate, 0.02 M sodium barbital, 0.15 M sodium chloride, 1 g/l bovine serum albumin and 0.15 g/l 8-anilino-1-naphtalenesulfonic acid, at pH 7.4) was then added to the tubes and the tubes were vortexed. 0.1 ml of the labeled anti-$T_3$ antibody prepared in A (~5×10⁶ RLU) in Buffer I minus barbital and 8-anilino-1-naphtalenesulfonic acid, was added to each tube, vortexed and incubated for 1 hour at room temperature. The tubes were then placed in a specially designed rack useful for magnetic separation of paramagnetic particles in test tubes (available from Ciba Corning Diagnostics Corp., Medfield, Mass.). The magnetic field separated the particles from the supernatant and the supernatant was then decanted. The particles were washed once in 1 ml of deionized water, vortexed, and magnetically separated. The particles were resuspended in 0.1 ml of deionized water. The signal was detected in a luminometer (MAGIC® Lite Analyzer, Ciba Corning Diagnostics Corp., Medfield, Mass.). 0.3 ml of a solution of 0.1% hydrogen peroxide in 0.1 N $HNO_3$ was added to each tube by the luminometer and the light emission was triggered by the addition of 0.3 ml of 0.25 N NaOH containing detergent. The measured RLU for each tube was plotted against its respective $T_3$ concentration as shown in FIG. 1.

Figure 2:
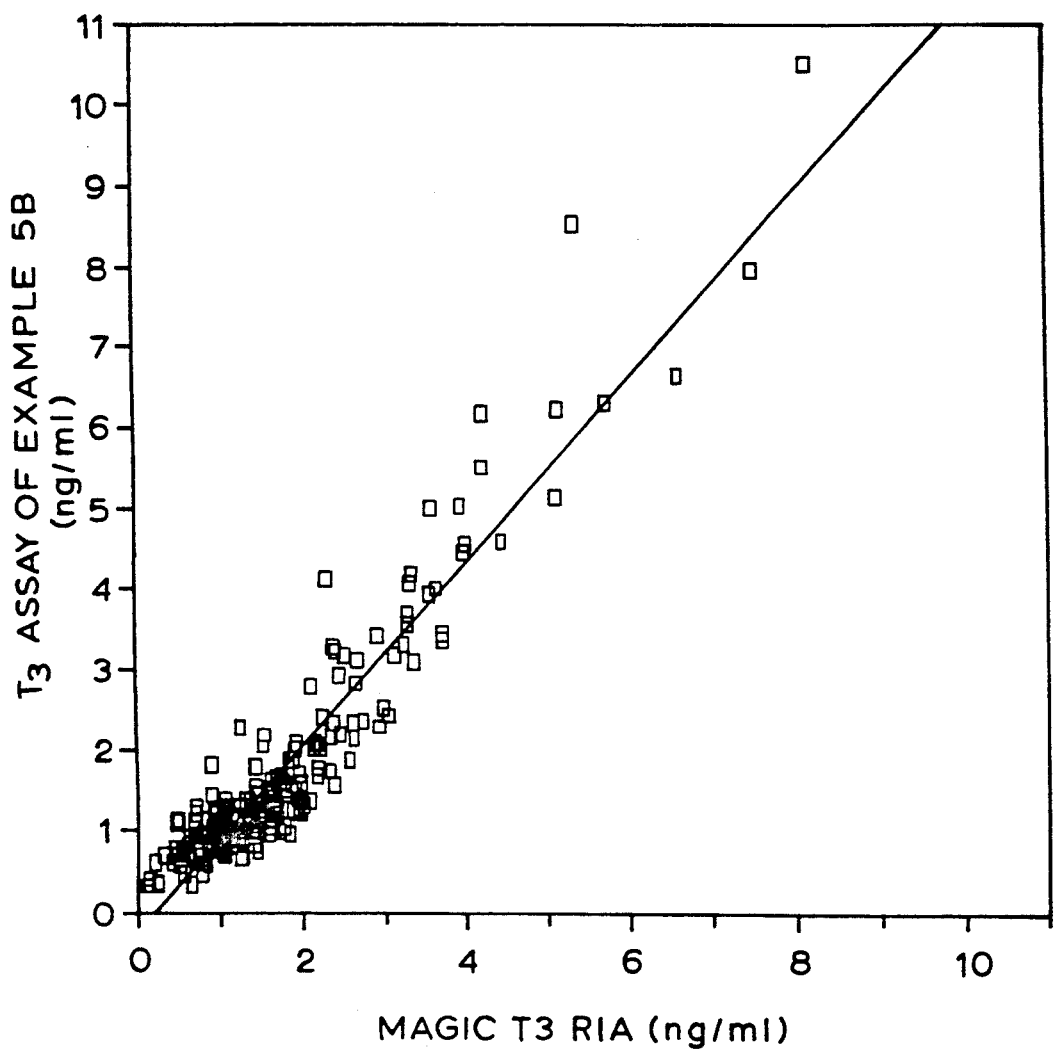
FIG. 2 is a plot of a regression analysis comparing the results obtained from a total $T_3$ assay of various samples using a commercial $T_3$ RIA kit and using the method of this invention.

C. 222 patient serum samples with $T_3$ values ranging from 0.2 to 8.3 ng/ml (as determined by radioimmunoassay [RIA]) were assayed by using the procedure described in B and by using a MAGIC® $T_3$ RIA kit according to the written protocol supplied with the kit. The results obtained were subjected to regression analysis and plotted (see FIG. 2). The coefficient of correlation between the results obtained using the procedure described in B and the results obtained using the MAGIC® $T_3$ RIA was 0.94 and the regression line had a slope of 1.15 and an intercept of -0.25 (see FIG. 2).

EXAMPLE 6

Assay for $T_4$ Using Immobilized Thyroglobulin

A. Monoclonal anti-$T_4$ antibody was produced in mice (A/J) by immunization with the BSA-$T_4$ conjugate and subsequent fusion of the splenocytes with Sp2/0-Ag 14 myeloma cells by the procedure described by Kohler and Milstein in Nature (London), Vol. 256, pp. 495–497 (1975). Hybridoma cells secreting anti-$T_4$ antibody were injected introperitoneally into pristane-primed mice (CAF). Ascitic fluid from these mice was collected after 3-5 weeks. The anti-$T_4$ antibody was purified from the ascitic fluid and labeled with acridinium ester according to procedures described in Example 5A for the anti-$T_3$ antibody.

Figure 3:
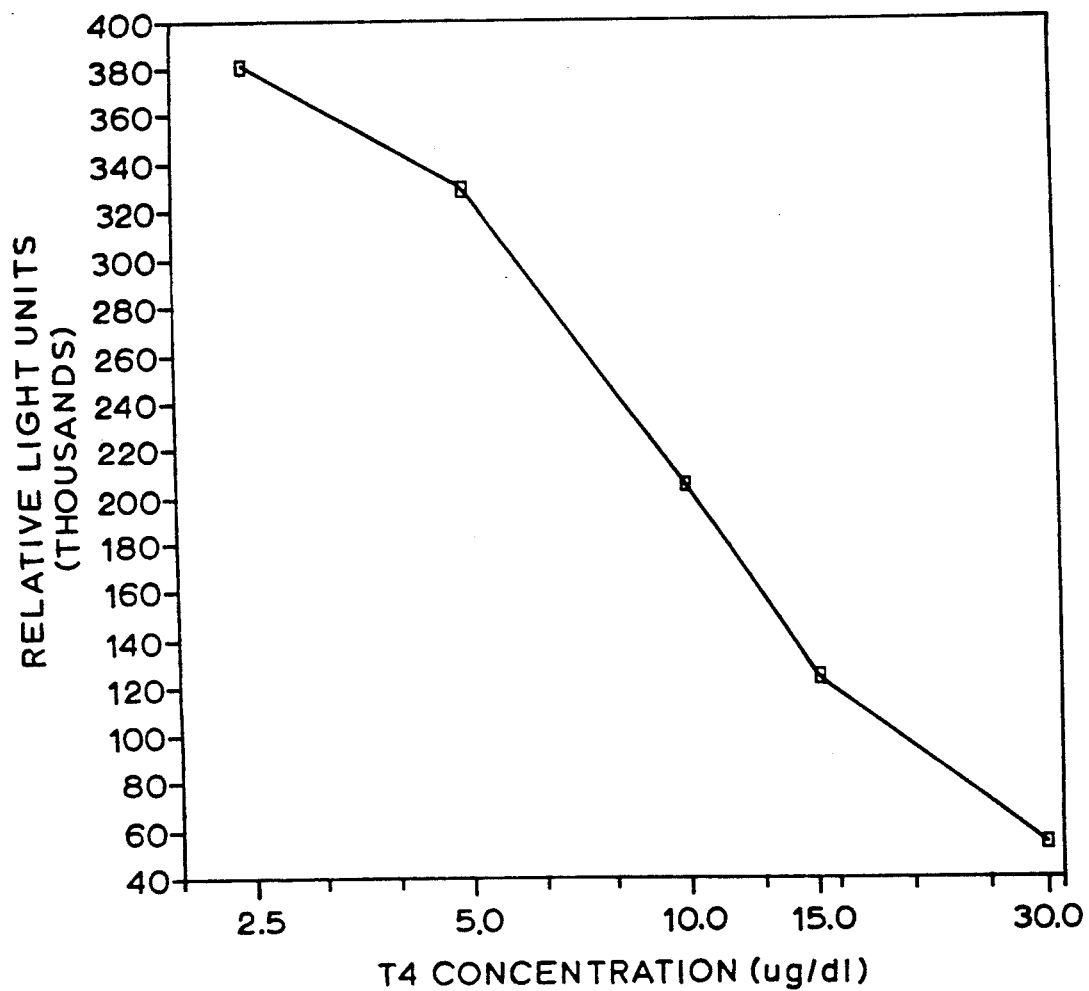
FIG. 3 is a standard curve of a total $T_4$ assay obtained using immobilized thyroglobulin and an acridinium ester labeled anti-$T_4$ antibody.

B. A series of standards (0.05 ml) with increasing amounts of $T_4$ were added to 12×75 mm plastic tubes. 0.5 ml of immobilized thyroglobulin prepared in Example 3 (5 mg/l in Buffer II containing 0.02 m sodium phosphate, 0.02 M sodium barbital, 0.15 M sodium chloride, 1 g/l BSA, 1 g/l sodium azide, 0.15 g/l 8-anilino-1-naphtalenesulfonic acid, at pH 7.4) was then added to each tube and vortexed. 0.1 ml of the labeled anti-$T_4$ antibody prepared in A (~5×10⁶ RLU in Buffer II minus barbital and ANS) was added to each tube, vortexed and incubated for 1 hour at room temperature. The sample in each tube was subjected to the same magnetic separation, washing and counting procedure described in Example 5B. The measured RLU for each tube was plotted against the respective $T_4$ concentration of each tube as shown in FIG. 3.

C. 53 patient serum samples with $T_4$ values ranging from 3.6 to 24.5 ug/dl (as determined by RIA) were assayed by the procedure described in B and by using a MAGIC® $T_4$ RIA Kit according to the written protocol supplied with the kit. The results were subjected to regression analysis and plotted. The coefficient of correlation between the results obtained using the procedure described in B and the results obtained using the RIA kit was 0.93 and the coefficient of variation was 5%.

EXAMPLE 7

Assay for Free-$T_3$ Using Immobilized Thyroglobulin

Figure 4:
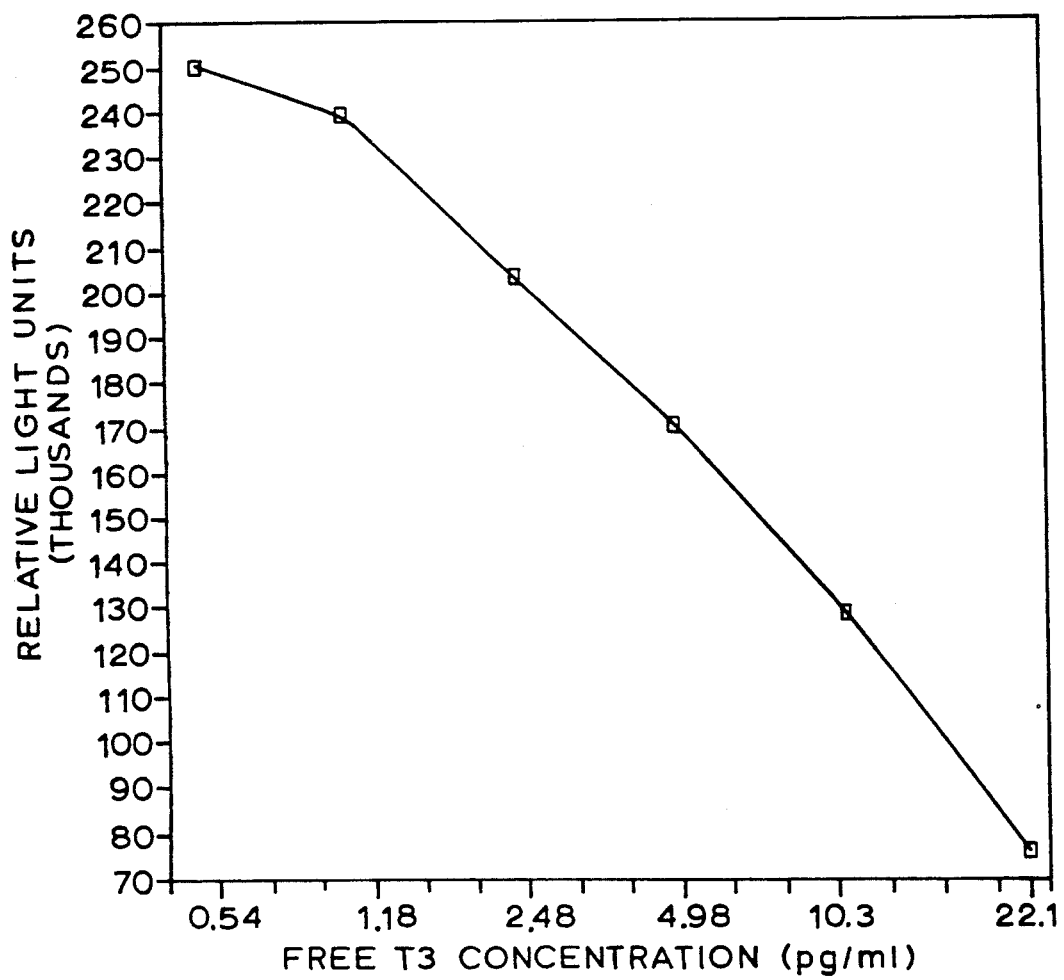
FIG. 4 is a standard curve of a free $T_3$ assay obtained using immobilized thyroglobulin and an acridinium ester labeled anti-$T_3$ antibody.

A. A series of standards (0.05 ml) (from a MAGIC® F-$T_3$ RIA kit, Ciba Corning Diagnostics Corp., Medfield, Mass.) with increasing amounts of free $T_3$ were added to 12×75 mm plastic tubes. 0.5 ml of the solid phase bovine thyroglobulin prepared in Example 3 (0.125 mg/l in Buffer III containing 0.02 M sodium phosphate, 0.02 M sodium barbital, 0.15 M sodium chloride, and 1 g/l BSA) was then added to the tubes and the tubes were vortexed. 0.1 ml of labeled anti-$T_3$ antibody prepared in Example 5A (~2.5×10$^6$ RLU) in Buffer III minus barbital, was added to each tube, vortexed and incubated for 1 hour at room temperature. The particles were separated, washed and counted as described in Example 5B. The measured RLU for each tube was plotted against its respective free $T_3$ concentration as shown in FIG. 4.

B. 76 patient serum samples with free-$T_3$ values ranging from 0.04 to 13.4 pg/ml (as determined by RIA) were assayed using the procedure described in A and using the MAGIC® F-$T_3$ RIA kit according to the written protocol provided with the kit. The results were subjected to regression analysis and plotted. The coefficient of correlation between the results obtained from the two procedures was 0.94 and the coefficient of variation was 18%.

EXAMPLE 8

Assay for Free $T_4$ Using Immobilized Thryoglobulin

Figure 5:
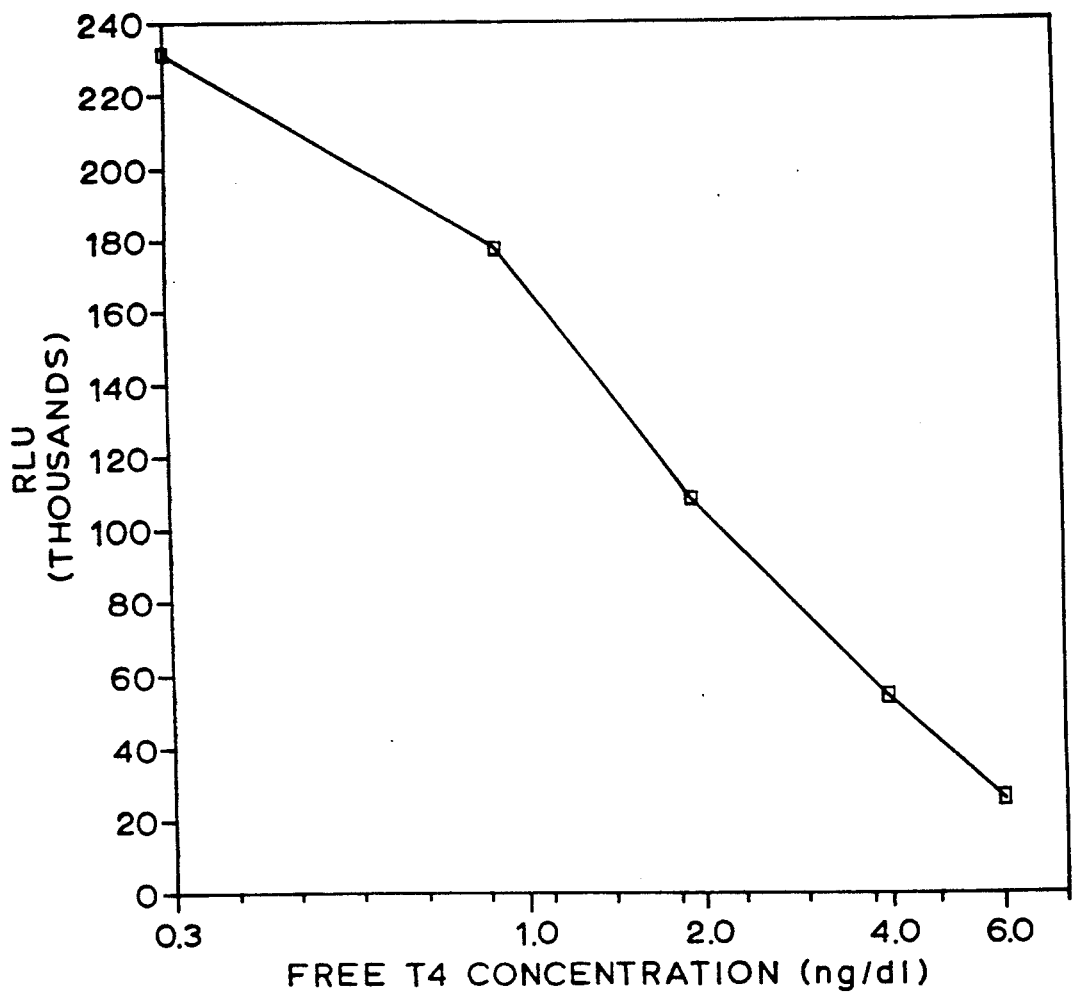
FIG. 5 is a standard curve of a free $T_4$ assay obtained using immobilized thyroglobulin and an acridinium ester labeled anti-$T_4$ antibody.

A. A series of standards (0.05 ml) (from a MAGIC® F-$T_4$ RIA kit, Ciba Corning Diagnostics Corp., Medfield, Mass.) with increasing amounts of free $T_4$ were added to 12×75 mm plastic tubes. 0.5 ml of the solid phase bovine thyroglobulin prepared in Example 3 (0.25 mg/ml in Buffer III containing 0.02 M sodium phosphate, 0.02 M sodium barbital, 0.15 M sodium chloride and 1 g/l BSA) was then added to the tubes and the tubes were vortexed. 0.1 ml of the labeled anti-$T_4$ antibody prepared in Example 6A (~5×10$^6$ RLU) in Buffer III minus barbital, was added to each tube, vortexed and incubated for 1 hour at room temperature. The particles were separated, washed and counted as described in Example 6B. The measured RLU for each tube was plotted against its respective free $T_3$ concentration as shown in FIG. 5.

Figure 6:
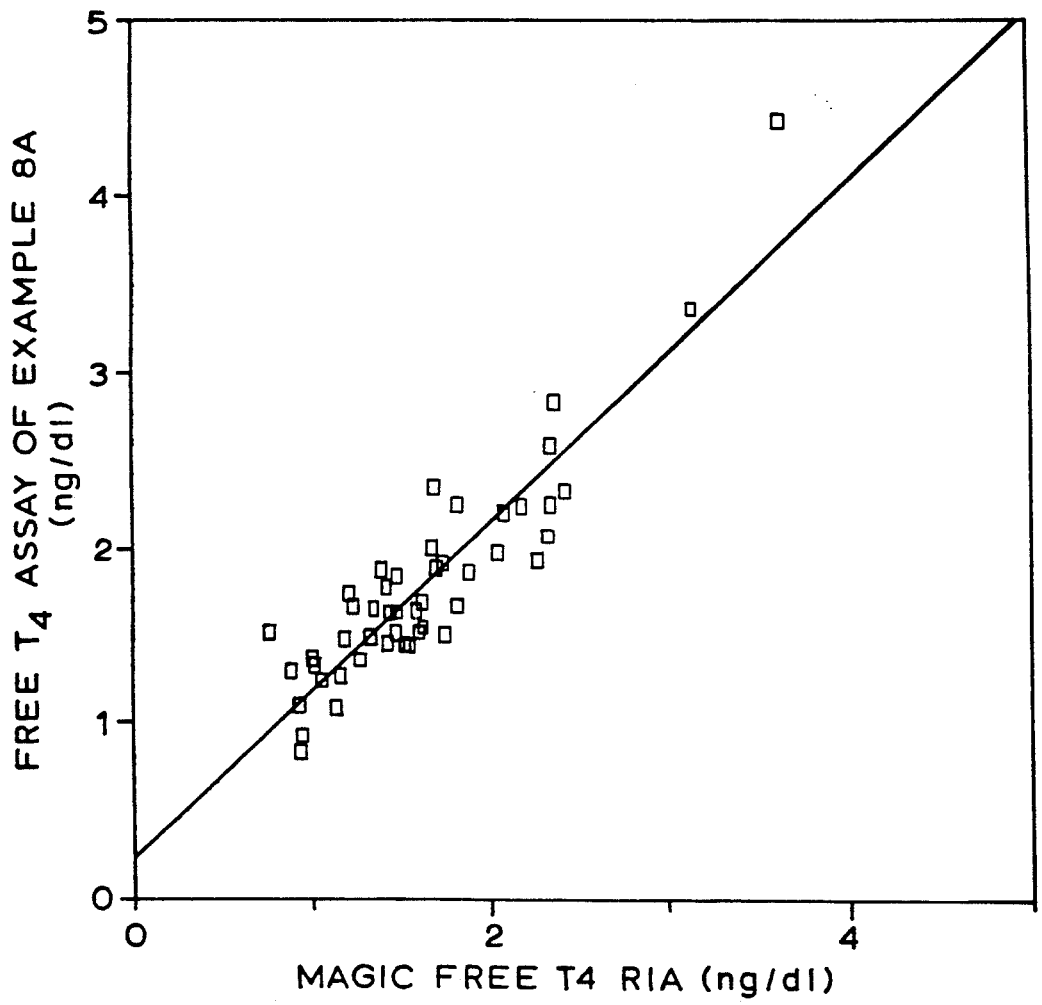
FIG. 6 is a plot of a regression analysis comparing the results obtained from a free $T_4$ assay of various samples using a commercial free-$T_4$ RIA kit and using the method of this invention.

B. 48 patient serum samples with free $T_4$ values ranging from 0.75 to 3.7 ng/dl (as determined by RIA) were assayed using the procedure described in A and using the MAGIC® F-$T_4$ RIA kit according to the written protocol provided with the kit. The results were subjected to regression analysis and plotted. The coefficient of correlation between the results obtained from the two procedures was 0.91 and the coefficient of variation was 4.3% (see FIG. 6).

EXAMPLE 9

Assay for T-Uptake Using Immobilized Thyroglobulin

A. Monoclonal anti-TBG antibody was produced in mice (A/J) by immunization with TBG and subsequent fusion of the splenocytes with Sp2/0-Ag 14 myeloma cells by the procedure described by Kohler and Milstein in Nature (London), Vol. 256, pp. 495-497 (1975). Hybridoma cells secreting anti-TBG antibody were injected introperitoneally into pristane-primed mice (CAF). Ascitic fluid from these mice was collected after 3-5 weeks. The anti-TBG antibody was purified using the Affi-Gel Protein A MAPS II kit (Bio-Rad Laboratories, Richmond, Calif. 94801) according to the written protocol provided with the kit. The purified antibody was labeled with acridinium ester according to the procedure described in Example 5A.

B. A series of standards (0.01 ml) (from a MAGIC® $T_3$-Uptake RIA kit, Ciba Corning Diagnostics Corp., Medfield, Mass.) with increasing $T_3$-Uptake ratios (see Table 1) were added to 12×75 mm polystyrene tubes. 0.5 ml of the solid phase bovine thyroglobulin prepared in Example 3 (10 ug/ml in 0.01 M sodium phosphate, pH 7.4) was then added to each tube and the tubes were vortexed. 0.1 ml of the anti-TBG antibody prepared in A (~7×10$^6$ RLU) in 0.01 M sodium phosphate, pH 7.4, was added to each tube, vortexed and incubated for 1 hour at room temperature. The particles were then separated, washed and counted as described in Example 5B. The results are listed in Table 1.

C. 19 patient serum samples with $T_3$-Uptake ratios ranging from 0.57 to 1.26 (as determined by RIA) were assayed using the procedure described in B and using the MAGIC® $T_3$-Uptake RIA kit according to the written protocol provided with the kit. The results were subjected to regression analysis and plotted. The coefficient of correlation between the results obtained from the two procedures was 0.85 and the coefficient of variation was 5.4%.

TABLE 1

| $T_3$-Uptake Ratios of Reference Serum And Control Sera | | |
|---|---|---|
| Serum | RLU | $T_3$-Uptake Ratio |
| Reference | 135,600 | 1 |
| Control A | 153,387 | 0.885 |
| Control B | 110,438 | 1.232 |
| Control C | 39,088 | 3.474 |

EXAMPLE 10

Stability of Immobilized Thyroglobulin

A. The solid phase immobilized thyroglobulin prepared as described in Example 3 was diluted in the Buffers described in Examples 5B and 6B to the concentrations described in Examples 5B and 6B, respectively, and heated at 37° C. for 7 days in plastic containers. The $T_3$ and $T_4$ assays described in Examples 5B and 6B were conducted using the heat treated particles.

B. $T_3$-ferritin, $T_3$-BSA, and $T_4$-BSA conjugates were prepared according to the method described in Anderson et al, J. Am. Chem. Soc. Vol 86, 1839 (1964). These conjugates were immobilized by the method described in Example 1 for thyroglobulin. These conjugates were also heated at 37° C. for 7 days. $T_3$ and $T_4$ assays were performed using these heat treated conjugates according to the procedures described in Example 5B and 6B substituting the immobilized conjugates for the immobilized thyroglobulin.

C. The results obtained from the assays of A and B are listed in Table 2. Loss of binding of labeled antibody occurred in all cases. However, use of the heated solid phase thyroglobulin resulted in only 5-10% loss as compared to 30-50% loss using the heated conjugates of B.

TABLE 2

Stability of Immobilized Conjugates

| Conjugate | % Loss of Binding After 7 Days at 37° C. |
|---|---|
| Test I | |
| BSA-$T_3$ | 50 |
| BSA-$T_4$ | 30 |
| Test II | |
| Ferritin-$T_3$ | 35 |
| Thyroglobulin ($T_3$ Assay) | 5 |
| Thyroglobulin ($T_4$ Assay) | 10 |

EXAMPLE 11

Assay for $T_3$ Using Labeled Thyroglobulin and Immobilized Antibody

A. Rabbit anti-$T_3$ antiserum was purified by ammonium sulfate percipitation and immobilized on paramagnetic particles as described in Example 1, substituting the purified antibody for the thyroglobulin.

Figure 7:
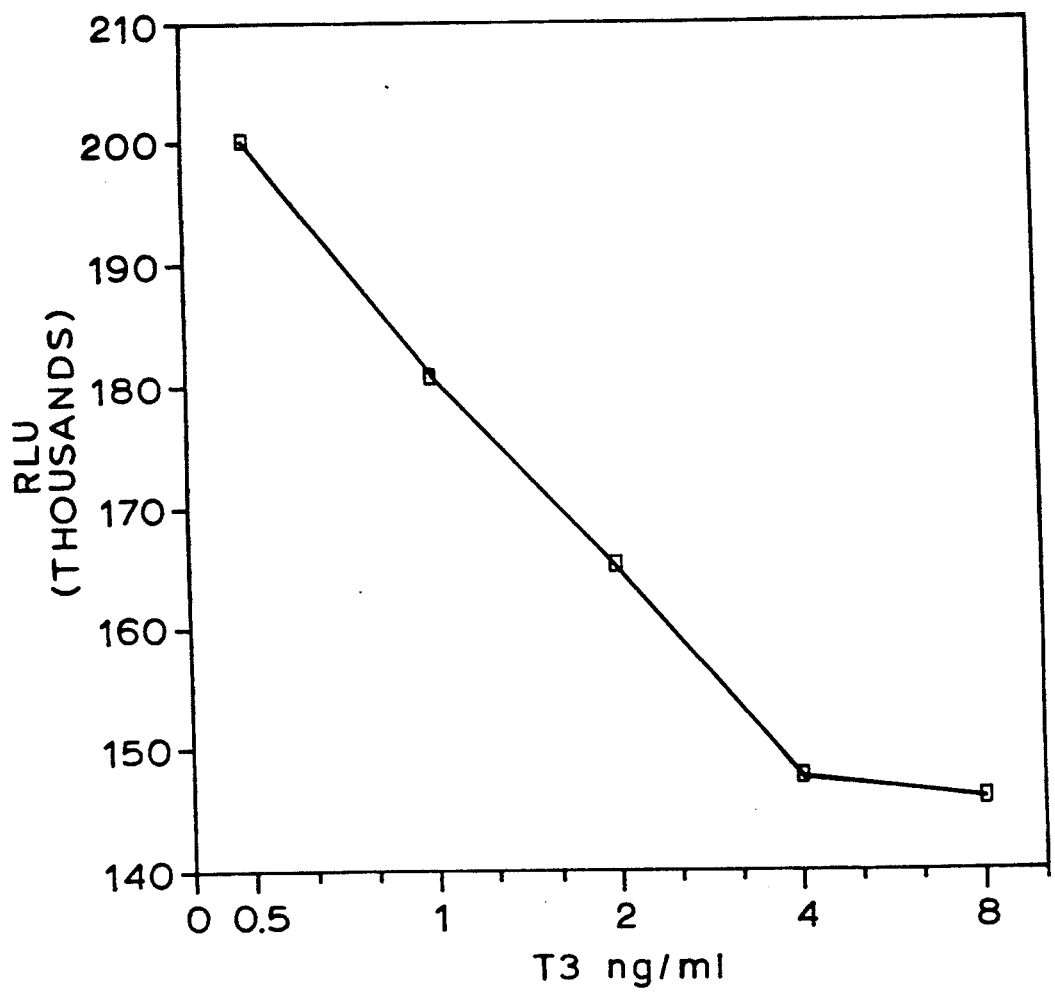
FIG. 7 is a standard curve of a total $T_3$ assay obtained using acridinium ester labeled thyroglobulin and immobilized anti-$T_3$ antibody.

B. A series of standards (0.05 ml) (from a MAGIC® $T_3$ RIA kit) with increasing amounts of $T_3$ were added to 12×75 mm plastic tubes. 0.5 ml of the immobilized anti-$T_3$ antibody prepared in A (diluted 1:1500 in the Buffer I of Example 5B) and 0.1 ml of the labeled thyroglobulin prepared in Example 4 ($\sim 6 \times 10^6$ RLU in the Buffer I of 5B minus barbital and ANS) were then added to the tubes, vortexed and incubated for 1 hour at room temperature. The resultant particles were then separated, washed and counted as described in Example 5B. The measured RLU for each tube was plotted against its respective $T_3$ concentration as shown in FIG. 7.

EXAMPLE 12

Assay for $T_4$ Using Labeled Thyroglobulin and Immobilized Antibody

A. Rabbit anti-$T_4$ antiserum was purified by ammonium sulfate percipitation and immobilized on paramagnetic particles as described in Example 1, substituting the purified antibody for the thyroglobulin.

Figure 8:
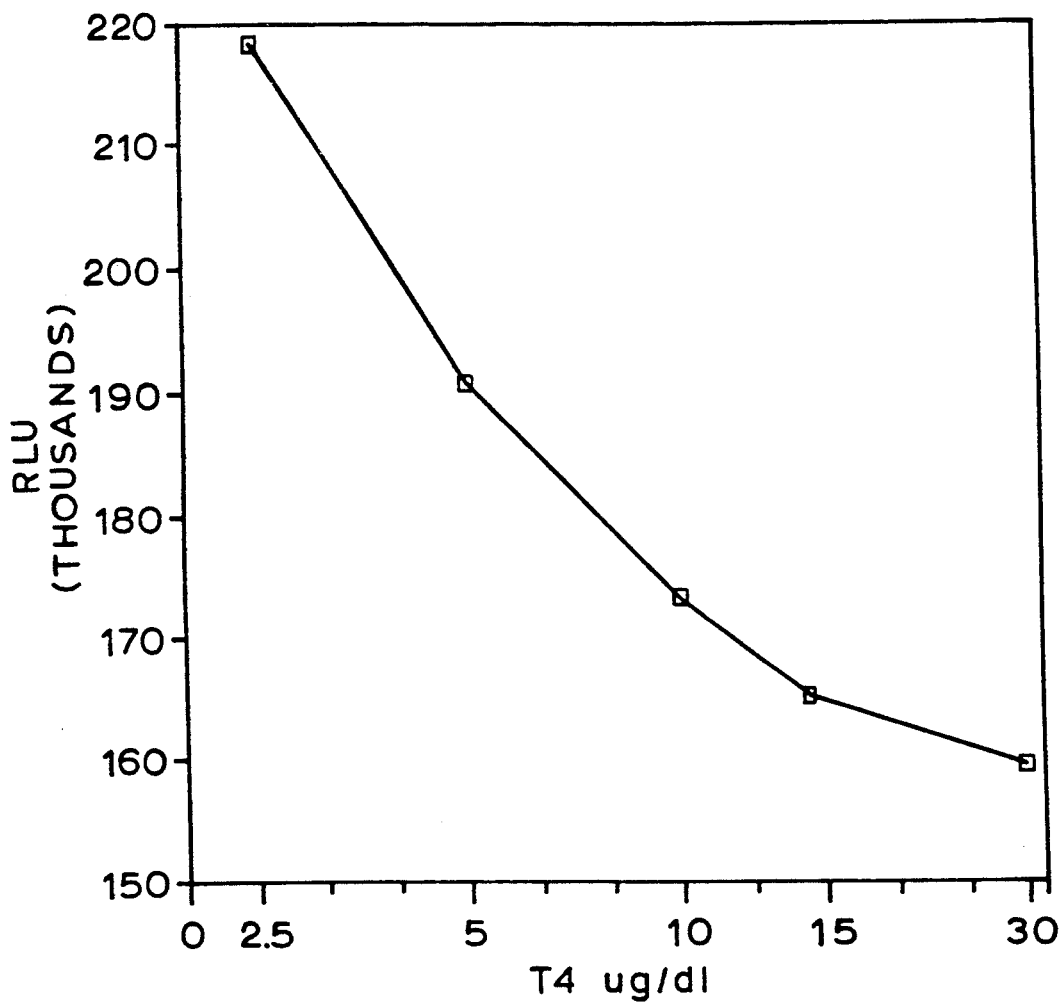
FIG. 8 is a standard curve of a total $T_4$ assay obtained using acridinium ester labeled thyroglobulin and immobilized anti-$T_4$ antibody.

B. A series of standards (0.05 ml) (from a MAGIC® $T_4$ RIA kit) with increasing amounts of $T_4$ were added to 12×75 mm plastic tubes. 0.5 ml of the immobilized anti-$T_4$ antibody prepared in A (diluted 1:1500 in Buffer II of Example 6B) and 0.1 ml of the labeled thyroglobulin prepared in Example 4 ($\sim 6 \times 10^6$ RLU in the Buffer II of 6B minus barbital and ANS) were then added to the tubes, vortexed and incubated for 1 hour at room temperature. The resultant particles described in Example 5B. The measured RLU for each tube was plotted against its respective $T_4$ concentration as shown in FIG. 8.

What is claimed is:

1. A method for measuring a thyroid hormone in a serum sample which comprises:
   a. incubating a serum sample with a labeled antibody to a thyroid hormone and a composite comprising a thyroglobulin chemically modified by succinic anhydride immobilized on an insoluble carrier material, to form a complexed composite;
   b. separating the complexed composite from unbound labeled antibody;
   c. measuring the amount of label associated with the complexed composite or associated with the unbound labeled antibody; and
   d. relating the measurement of step c. to the amount of the thyroid hormone in the serum sample.

2. A method for measuring a thyroid hormone in a serum sample which comprises:
   a. incubating a serum sample with labeled thyroglobulin chemically modified by succinic anhydride and a composite comprising antibody to a thyroid hormone immobilized on an insoluble carrier material, to form a complexed composite;
   b. separating the complexed composite from unbound labeled thyroglobulin;
   c. measuring the amount of label associated with the complexed composite or associated with the unbound labeled thyroglobulin; and
   d. relating the measurement of step c. to the amount of the thyroid hormone in the serum sample.

* * * * *